United States Patent
Heckele et al.

(10) Patent No.: US 6,176,855 B1
(45) Date of Patent: Jan. 23, 2001

(54) ENDOSCOPIC INSTRUMENT FOR THE THERAPY OF THE HEART MUSCLE

(75) Inventors: Helmut Heckele, Knittlingen; Martin Seebach, Oberderdingen; Friedrich-Wilhelm Hehrlein, Giessen; Reinhard Schueck, Wetzlar, all of (DE)

(73) Assignee: Richard Wolf GmbH, Knittlingen (DE)

( * ) Notice: Under 35 U.S.C. 154(b), the term of this patent shall be extended for 0 days.

(21) Appl. No.: 09/172,330

(22) Filed: Oct. 14, 1998

(30) Foreign Application Priority Data

Oct. 15, 1997 (DE) .............................................. 197 45 488

(51) Int. Cl.⁷ .................................................... A61B 18/18
(52) U.S. Cl. .................. 606/15; 606/7; 606/16; 600/106; 600/153
(58) Field of Search ............................... 606/2, 7, 10, 13, 606/15, 16; 600/106, 104, 114, 153, 156

(56) References Cited

U.S. PATENT DOCUMENTS

| | | | |
|---|---|---|---|
| 4,874,371 | * 10/1989 | Comben et al. | 600/106 |
| 4,976,710 | * 12/1990 | Mackin | 606/15 |
| 5,188,634 | * 2/1993 | Hussein et al. | |
| 5,203,781 | * 4/1993 | Bonati et al. | 600/153 |
| 5,554,152 | 9/1996 | Aita et al. | |
| 5,725,523 | * 3/1998 | Mueller | 606/15 |
| 5,733,277 | * 3/1998 | Pallarito | |
| 5,843,105 | * 12/1998 | Mathis et al. | 606/166 |
| 5,860,968 | * 1/1999 | Wojcik et al. | |
| 6,027,497 | * 12/1998 | Daniel et al. | 606/15 |

FOREIGN PATENT DOCUMENTS

| | | |
|---|---|---|
| 2877268 | 7/1977 | (DE) . |
| 94 06 577 | 10/1994 | (DE) . |
| 195 37 084 | 4/1997 | (DE) . |
| 0 792 624 | 9/1997 | (EP) . |

* cited by examiner

Primary Examiner—Linda C. M. Dvorak
Assistant Examiner—Bryan K. Yarnell
(74) Attorney, Agent, or Firm—Cohen, Pontani, Lieberman & Pavane

(57) ABSTRACT

An endoscopic instrument for the therapy of the heart muscle forming channels in the heart muscle tissue by way of laser energy and including a shank tube and at least one instrumentation channel for a laser fiber disposed in axial direction within the shank tube as well as central optics parallel to the laser fiber for observing the locus of treatment. The distal end of the shank tube may be connected to a vacuum source and is designed such that the heart muscle can be restrained by partially suctioning the same against the shank end.

11 Claims, 2 Drawing Sheets

ENDOSCOPIC INSTRUMENT FOR THE THERAPY OF THE HEART MUSCLE

BACKGROUND OF THE INVENTION

The present invention relates to an endoscopic instrument for the therapy of the heart muscle, in which by way of laser energy channels are incorporated into the heart muscle.

In heart muscle therapy which is described in an abbreviated manner with TMR (transmyocardial revascularization) by way of laser energy several channels are drilled into the heart muscle temporally between the heart beats, when the heart chamber is filled with blood. In this way in the course of time blood may enter into the channels by which means the heart muscle may be supplied with blood enriched with oxygen. At the same time new vessels are formed in the heart muscle.

Amongst physicians there is the great desire to be able to carry out this therapy with minimal-invasive surgery. Since this is effected at the beating heart, a local restraining of the heart muscle must be achieved.

BRIEF SUMMARY OF THE INVENTION

It is therefore an object of the present invention to provide an instrument with which in a simple and gentle manner by way of laser energy a number of channels can be incorporated into the partially restrained heart muscle with a visual control. This object is achieved by an instrument having a shank tube and at least one instrumentation channel for a laser fiber; an optical system for observing the locus of treatment is preferably disposed within the central axis of the shank tube. A vacuum is applied to the distal end of the shank tube and to the locus of treatment so as to suction the instrument against the heart muscle thereby at least partially restraining the heart muscle.

With the instrument according to the present invention in a simple manner a number of channels may be incorporated in the heart muscle which is partially restrained in a gentle manner. This way an improved flow of blood and an improved oxygen supply of the heart muscle tissue is achieved without laying the hitherto customary bypasses. Furthermore the operational time and costs may be considerably reduced with this minimal invasive instrumentation.

Preferably the instrumentation channel of the laser fiber lies eccentrically to the longitudinal axis of the shank tube as well as of the optics running centrically through the shank tube, and the instrumentation channel and the optics are rotatable in the shank tube as a so that within a certain heart muscle region a defined number of channels may be placed into the heart muscle by simple rotation of the eccentrically arranged instrumentation channel.

It is advantageous that the optics have an exit view which is directed slightly laterally. In this way it is achieved that the optical axis and the axis of the operating channel meet at a defined distance.

In an alternative embodiment the endoscopic instrument according to the present invention is provided with several instrumentation channels which are arranged preferably evenly distributed about the optics running centrically through the shank tube wherein the instrument channels and the optics together are rotatable as a single unit in the shank tube. Accordingly, by rotating of the instrumentation channels about the optical axis a simplification of the method can be achieved and yet in a simple manner several channels may be placed into the heart muscle within a certain surface area.

With the instrument according to the present invention it is further advantageous when the optics and each instrument channel can be axially adjusted in the shank tube together.

The distal end region of the shank tube which can be set under vacuum is elastic in a preferred embodiment of the present invention, i.e. it is rubber-elastically deformable so that this end region e.g. may assume the shape of a suction bell with which the heart wall may be locally suctioned with a vacuum under elastic deformation of the suction bell and thus at least partially restrained without danger of injury.

In an alternative embodiment the distal end region of the shank tube may comprise one or more lateral openings whilst the end face of the distal shank tube end comprises a tubular vacuum channel which is open on the side of the organ for suctioning the heart muscle surface. Furthermore the laser fiber within the instrumentation channel and each instrumentation channel may be axially adjustable in the shank tube.

BRIEF DESCRIPTION OF THE DRAWINGS

The present invention is hereinafter described in more detail by reference to the drawing in which.

DETAILED DESCRIPTION OF THE INVENTION

Figure 1:
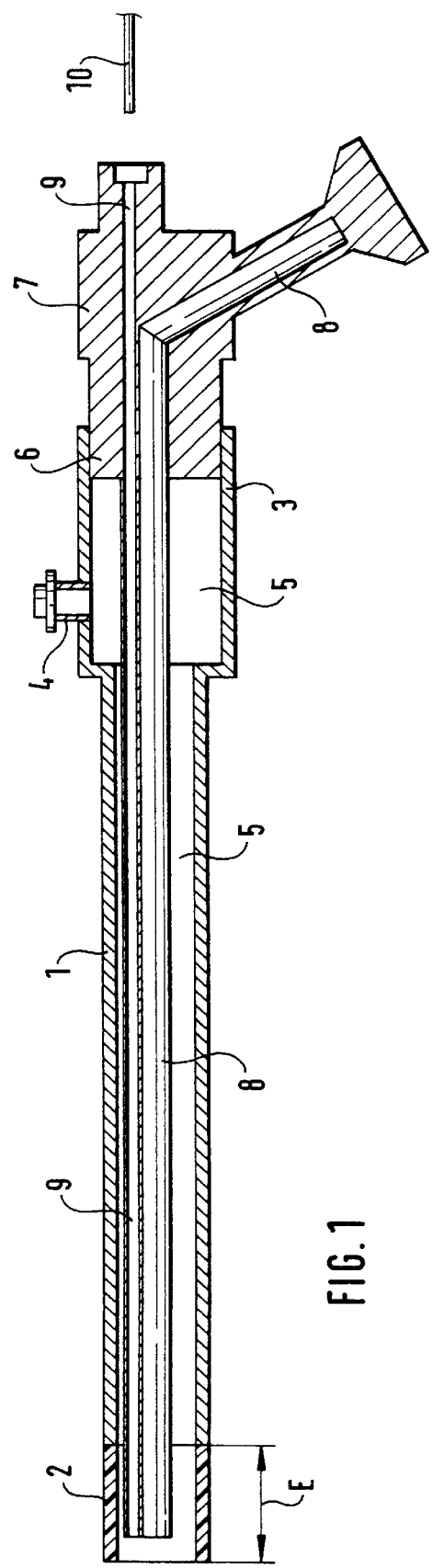
FIG. 1 is a schematic in longitudinal sectional lateral view of an instrument according to the present invention.

The endoscopic instrument according to FIG. 1 consists of a shank tube 1 which comprises at its distal end an elastic region 2 of a certain length E and which on the proximal side is provided with a cylindrical receiver 3 which has a connection piece 4 to be connected to a vacuum source so as to apply a vacuum to so as to apply the free space 5 located in the shank 1 can be impinged by a vacuum.

Into the end 6 of the receiver 3, which is firstly open on the proximal side, there may be introduced an operating insert 7 which comprises an optical system or optics 8 as well as at least one axially running instrumentation channel 9, and which is axially displaceable within the free space 5 and is rotatable about the instrument longitudinal axis. A laser fiber 10 can be guided distally through the instrumentation channel such that the optical axis of the fiber lies parallel to the optical axis of the optics 8 located in the shank tube 1.

Figure 2:
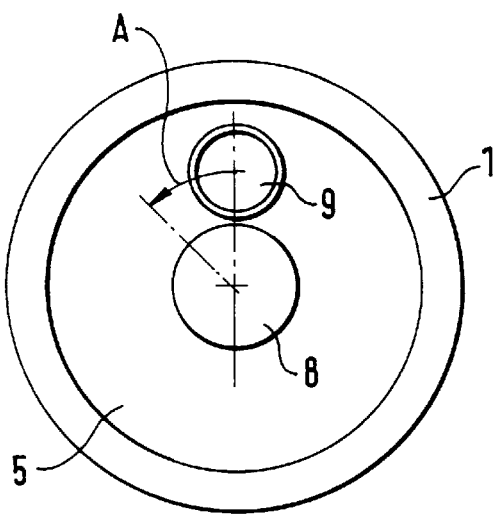
FIG. 2 is a view of the distal end face of a first embodiment of an endoscopic instrument of the present invention.

From FIG. 2 can to be seen that the optical system 8 and the instrumentation channel 9 through which the laser fiber indicated in FIG. 1 at 10 can be guided, are arranged parallel to one another and are commonly rotatable about the optical axis of the system 8 (arrow A).

Figure 3:
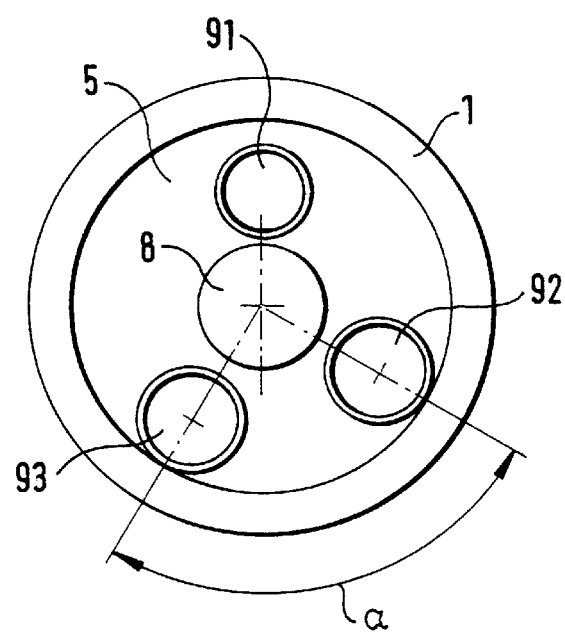
FIG. 3 is a view of the distal end face of a second embodiment of an endoscopic instrument of the present invention and FIG. 4 is a schematic and partly sectional perspective view of the distal end section of a third embodiment of an instrument according to the present invention for placing channels into the heart muscle.

In the embodiment shown in FIG. 3 instead of the instrumentation channel 9 shown in FIG. 2 there are provided three channels 91, 92, 93 which are uniformly arranged about the optics 8 with an angular distance α to one another.

Similar as with the instrument according to FIG. 2 the three instrument channels 91, 92, 93 according to FIG. 3 may also be rotatable about the axis of the optics or of the optical system 8. However, also with a rigid arrangement of the instrumentation channels 91, 92, 93 about the optics a simplification of the method is achieved.

Figure 4:
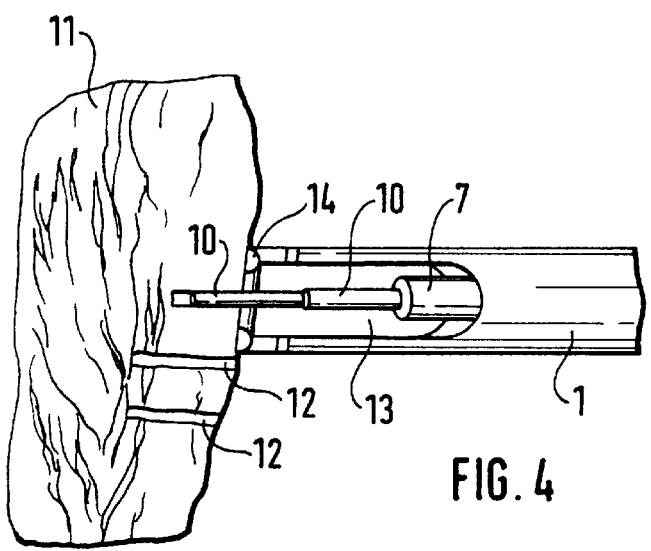

FIG. 4 shows the application of the instrument under direct visual control as well as two channels 12 already incorporated into the heart muscle 11 by laser energy.

Since the distal end of the shank tube 1 comprises lateral openings 13 which permit a good observation of the tissue section to undergo therapy via the optics, at the end face shank tube end there is located an annular vacuum channel 14 which is open on the side of the organ and with which the instrument may be fixed to the surface of the organ for positional fixation by suction. The vacuum channel 14 which in this case may be formed by the inner space of an elastic ring element, may e.g. be connected to a vacuum source via a channel provided in the shank tube or provided internally on the shank tube.

In order to incorporate a certain number of channels into the heart muscle tissue, the distal instrument end is guided through a trocar sleeve into the abdominal cavity and subsequent thereto is guided so far onto the organ until the instrument end bears on the surface of the organ and by way of this the end face opening or the annular channel 14 according to FIG. 4 is closed. At the inner or free space 5 which is then closed or the annular channel 14 a vacuum may then be applied so that the instrument is sucked onto the surface of the organ in a position-stable manner and here the heart muscle is restrained.

Subsequent to the alignment and fixing of the instrument a laser fiber 10 may be guided through the instrumentation channel 9 according to FIG. 2 or the instrument channels 91, 92, 93 according to FIG. 3 or through the instrument channel according to FIG. 4 up to the organ and by way of leading through laser light of a high energy intensity a channel may be incorporated into the heart muscle tissue. At the same time the embodiment shown in FIG. 3 permits a simultaneous incorporation of three channels without the instrumentation channels having to be rotated.

As soon as a number of channels has been incorporated into the organ section which has been suctioned once, the vacuum may be removed and the instrument may be again applied to a different location in the same manner and again a number of channels may be incorporated into the heart muscle. Each time by way of the suction effect at the end face of the instrument a local restraining of the tissue is effected so that the incorporation of the channels by the laser beam may be quickly carried out locally in an exact manner and with a visual control. The invention is not limited by the embodiments described above which are presented as examples only but can be modified in various ways within the scope of protection defined by the appended patent claims.

What is claimed is:

1. An endoscopic instrument for forming one or more channels in the heart muscle tissue by laser energy, comprising:

a shank tube having a longitudinal axis and at least one instrumentation channel, a laser fiber disposed within said channel and an optical system within said shank tube for observing a locus of treatment, said shank tube having a distal end region and integral therewith a means for applying a vacuum in said distal end region to the locus of treatment so as to suction the instrument against the heart muscle thereby at least partially restraining the heart muscle, said instrumentation channel being arranged eccentrically to said longitudinal axis of said shank tube and rotatable therein with respect to the longitudinal axis.

2. The instrument according to claim 1, wherein said shank tube defines a free inner space and wherein a vacuum is applied to said inner space.

3. The instrument according to claim 1, wherein said optical system runs centrally through said shank tube and wherein said instrumentation channel and said optical system are rotatable in said shank tube as a unit.

4. The instrument according to claim 1, wherein said optical system has a laterally aligned exit view.

5. The instrument according to claim 1, wherein said optical system is disposed centrally with said shank tube and further comprising a plurality of instrument channels aligned about said centrally disposed optical system.

6. The instrument according to claim 5, wherein said instrumentation channels and said optical system are rotatable as a unit in said shank tube.

7. The instrument according to claim 6, wherein said optical system and said instrumentation channel are commonly axially adjustable in said shank tube.

8. The instrument according to claim 1, wherein said distal end region of said shank tube is elastically deformable.

9. The instrument according to claim 8, wherein said optical system and instrumentation channels are commonly axially adjustable in said shank tube.

10. The instrument according to claim 8, wherein said distal end region of said shank tube comprises one or more lateral openings and a distal end where an annular, distally open vacuum channel is disposed.

11. The instrument according to claim 1, wherein said distal end region of said shank tube comprises one or more lateral openings and a distal end where an annular, distally open vacuum channel is disposed.

* * * * *